Figure 1:
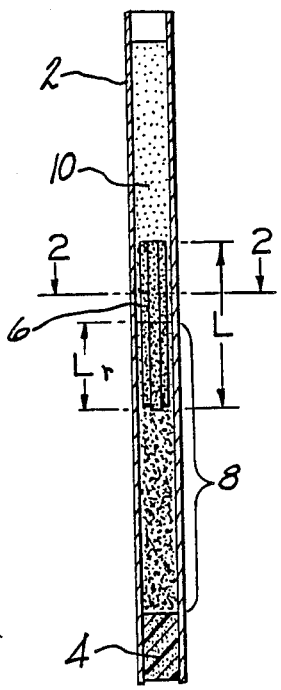

United States Patent [19]

Levine et al.

[11] Patent Number: 4,875,364

[45] Date of Patent: Oct. 24, 1989

[54] METHOD FOR MEASURING HEMOGLOBIN

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 333,265

[22] Filed: Apr. 5, 1989

Related U.S. Application Data

[63] Continuation of Ser. No. 170,771, Mar. 21, 1988, Pat. No. 4,843,869.

[51] Int. Cl.[4] .......................... B01D 21/26; A61B 5/14
[52] U.S. Cl. .................................. 73/61.1 R; 73/61.4; 436/70
[58] Field of Search .................... 73/61.4, 61.1 R, 149, 73/53; 128/637, 638, 771; 422/68, 55, 58, 59; 210/927, 787; 436/70, 63, 177; 494/10, 16

[56] References Cited

U.S. PATENT DOCUMENTS

| | | | |
|---|---|---|---|
| 4,027,660 | 6/1977 | Wardlaw et al. | 73/149 X |
| 4,082,085 | 4/1978 | Wardlaw et al. | 73/61.1 R |
| 4,137,755 | 2/1979 | Wardlaw et al. | 73/61.1 R |
| 4,181,609 | 1/1980 | Wardlaw et al. | 210/774 |
| 4,567,542 | 2/1986 | Wardlaw et al. | 73/61.1 R |
| 4,774,965 | 10/1988 | Rodriguez et al. | 73/61.1 R |

Primary Examiner—Hezron E. Williams
Attorney, Agent, or Firm—William W. Jones

[57] ABSTRACT

A whole blood sample is placed in a tube such as a capillary tube, with a plastic float. The float is axially elongated and has a specific gravity which causes it to float in the packed red blood cells when the sample is centrifuged in the tube. The hemoglobin concentration of the packed red blood cells is measured by measuring the depth that the float sinks into the red cell layer, and then the hemoglobin concentration of the blood is calculated. The hemoglobin can be measured in this manner because virtually the only red cell component which contributes density to the red cells is the hemoglobin. The hemoglobin concentration of the whole blood is calculated by multiplying the mean corpuscular hemoglobin concentration of the packed red blood cells by the packed cell volume % (hematocrit) of the whole blood. All of the necessary calculations may be performed by a preprogrammed microprocessor.

1 Claim, 1 Drawing Sheet

U.S. Patent  Oct. 24, 1989  4,875,364

METHOD FOR MEASURING HEMOGLOBIN

This is a continuation of copending application Ser. No. 07/170,771, filed Mar. 21, 1988, now U.S. Pat. No. 4,843,869.

This invention relates to a simple procedure for measuring the hemoglobin concentration in a sample of whole blood, and more particularly to a procedure which can be quickly performed by a relatively unskilled technician.

Two measurements commonly performed on the whole blood are the hematocrit and hemoglobin. The hematocrit is the percentage volume that packed red blood cells occupy in a centrifuged sample of whole blood, and the hemoglobin content is the weight of the hemoglobin per unit volume of whole blood. The numeric ratio of hemoglobin to hematocrit is referred to as the mean corpuscular hemoglobin concentration (MCHC), and in normal individuals it is close to 33.9%. When an individual is suffering from certain diseases, however, the ratio may vary from about 38% down to 26%. Thus, the determination of both the hematocrit and hemoglobin are important for the discovery and diagnosis of anemia or other blood disorders.

In a large laboratory the measurements of hematocrit and hemoglobin are usually made concurrently in an automated analyzer, but in a small clinic or in a physician's office, they must be made separately, using two different techniques. The hematocrit may be presently performed by filling a small bore glass tube with anticoagulated whole blood, sealing one end of the tube, and centrifuging the tube to pack the red blood cells. After packing, which takes about three to five minutes in a small centrifuge, the length of the packed red blood cell column and the total filled length are measured, and the hematocrit, expressed as a percentage, is calculated. It can be appreciated that little skill is required to prepare the tube or take the measurements. U.S. Pat. Nos. 4,027,660 issued June 7, 1977 to S. C. Wardlaw et al; 4,181,609 issued Jan. 1, 1980 to S. C. Wardlaw et al; 4,156,570 issued May, 1978 to S. C. Wardlaw; and 4,558,947 issued Dec. 17, 1985 to S. C. Wardlaw, and others describe a procedure which involves drawing a sample of anticoagulated whole blood into a capillary tube, placing a float in the tube with the blood sample, and centrifuging the blood sample to cause the float to settle into the red cell layer to elongate the buffy coat in the blood sample. This prior art technique can be used to measure hematocrit as well, by merely taking into account the expansion of a portion of the blood sample by the float when calculating the total length of the blood components, the observed total length being scaled down by the measuring instrument to compensate for the presence of the float.

On the other hand, the measurement of the hemoglobin concentration is considerably more complicated. To perform this test, in a small clinic or physician's office, the blood sample must be more accurately diluted to a ratio of either 1:250 or 1:500, depending on the equipment used. The dilution is made by accurately taking a tiny sample of the blood into a pipette and delivering it into a container containing an agent which dissolves the red blood cells, and cyanide, which converts the hemoglobin to a more easily measurable form. This mixture, after standing for three to ten minutes, is then placed in a photometer where the light attenuation at 560 nm (green) is compared to that of standard solutions. From these comparisons, the concentration of hemoglobin can be calculated. There are many published variations of this method, but all acceptable means to date require the accurate measurement of the light attenuation in an instrument designed for this purpose. Further, the need for accurately handling small quantities of the sample requires a higher level of skill than does the performance of the hematocrit, and is therefore also a source for analytical errors.

We have discoverd a procedure for measuring hemoglobin in a blood sample using basically the same paraphenalia and instruments which are presently used to measure hematocrit. Our procedure is based on our discovery that the hemoglobin concentration of the packed red blood cells is inversely proportional to the depth to which the float of the prior art sinks into the red cell layer. The microprocessor in the measuring instrument will be programmed to convert additional depth measurements into the hemoglobin concentration. The process steps used to perform the procedure of this invention are as follows. The whole blood sample is drawn into the centrifuge tube, preferably a capillary tube, anticoagulated, and the float is positioned in the tube. After the bottom of the tube is plugged, the sample is centrifuged so as to layer out the blood onto red cell, buffy coat, and plasma layers. During centrifugation, the float settles into the red cell layer. The hematocrit will then be measured generally as per the prior art.

The hemoglobin is measured as follows. As stated above, the MCHC of the red blood cells is the concentration of hemoglobin within them, normally about 340 g/l. Therefore, about ⅓ of each cell is hemoglobin, the rest is water and a small concentration of salts and minor proteins of relatively constant concentration. It follows from this that virtually the sole contributor to density differences between different patient's red blood cells is their hemoglobin concentration. Therefore, the packed red blood cell density is proportional to the MCHC, and if this value (MCHC) can be accurately obtained, the hemoglobin content can be calculated as: Hemoglobin=Hematocrit X MCHC.

The apparatus of the invention comprises a transparent tube of constant bore diameter, into which is placed a resinous float. Anticoagulated blood is drawn into the tube, either by capillary action or by slight suction. The exact quantity is not critical, as long as there is sufficient blood to buoy the float. One end of the tube is sealed, and the tube is then centrifuged at approximately 10,000 G's for approximately five minutes. This is the same regimen that is currently used to perform the standard hematocrit determination. When the centrifugation is complete, the float, which has a specific gravity between that of plasma and that of the packed red blood cells, will be partially buoyed up by the packed red blood cells. The hematocrit is measured by taking the ratio between the length of the blood sample in the tube (the total length of the packed red blood cells, buffy coat, and plasma) and the length of the packed red blood cell column only. The volume of the float must, of course, be accounted for in making this calculation. Because the depth of the float is inversely proportional to the density of the packed red blood cells, the red blood cell density may be calculated and converted to hemoglobin content as follows.

The sum of the buoyant forces on a floating object that has reached equilibrium, such as the float used in this invention, are zero. The buoyant forces in a three phase system such as ours which consists of a cylindrical plastic float; packed red blood cells; and plasma can be expressed as follows:

$$(D_r - D_f) \times L_r + (D_p - D_f) \times L_p = 0$$

wherein $D_r$ is the density of the packed red blood cells; $D_f$ is the density of the plastic float; $L_r$ is the length of the float which is submerged in the packed red blood cells; $D_p$ is the density of the plasma; and $L_f$ is the length of the float which is submerged in the plasma.

In the aforesaid equation, the density of the packed red blood cells is not known. The density and length of the plastic float are known, and are inputted into the microprocessor memory. Likewise, the density of the plasma is known and is inputted into the microprocessor memory. The length of the float which is submerged in the red blood cells is measured and is thus inputted into the microprocessor. Finally, the length of the float which is submerged in the plasma is calculated by the microprocessor by subtracting the length of the float submerged in the red blood cells from the total length of the float. The microprocessor can thus solve the equation for the density of the red blood cells ($D_r$).

Once $D_r$ has been calculated, MCHC can be calculated by the microprocessor by solving the following equation:

$$MCHC = (D_r \times K_s) + K_o$$

The MCHC constants, $K_o$ and $K_s$, may be determined empirically by taking red blood cell density measurements for a number of diverse samples and correlating the density with the MCHC as determined by conventional reference measurements. The slope constant ($K_s$) and the offset constant ($K_o$) of the best-fit correlation equation are then used to calculate the MCHC from the red blood cell density. Once calculated, $K_s$ and $K_o$ will not be changed unless the critical parameters of the paraphenalia, ie float density, etc. are changed.

From the MCHC, the hemoglobin concentration may be determined as previously described, ie, Hemoglobin = Hematocrit X MCHC.

It is therefore an object of this invention to provide an improved procedure for measuring the hemoglobin content in a sample of whole blood.

It is an additional object of this invention to provide a procedure of the character described wherein the hemoglobin content is measured as a function of the extent to which a float sinks into the packed red cell layer of a centrifuged blood sample contained in a tube.

It is a further object of this invention to provide a procedure of the character described wherein the hemoglobin and hematocrit measurements can be made quickly and easily with, or without, the use of an automatic computing device.

Figure 2:
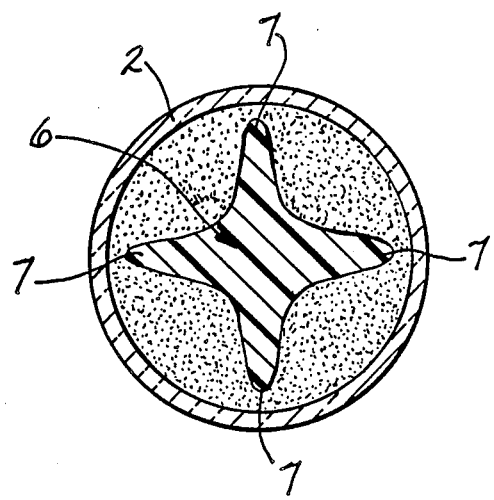

These and other objects and advantages of the invention will become more readily apparent from the following detailed description thereof when taken in conjunction with the accompanying drawings, in which:

FIG. 1 is a side elevational view of a glass tube containing a centrifuged blood sample and a float which has settled into the red blood cell layer of the centrifuged blood sample; and FIG. 2 is a cross sectional view of the tube taken along line 2—2 of FIG. 1.

Referring to the drawings, the tube 2 is preferably a glass capillary tube which may have an anticoagulant coated on its inside bore wall. The bottom of the tube 2 is closed off with a clay plug 4 or with a plastic cap which can be snapped over the end of the tube 2 after the blood sample is drawn into the tube 2. The float 6 is placed in the tube 2, and when the blood sample is centrifuged in the tube 2, the float 6 settles into the red cell layer, which is designated by the numeral 8. Above the float 6 is the plasma layer 10. The float 6 will have a preset known axial length L, and the technician taking the measurements will measure the distance $L_r$, which is the length of the float 6 which has sunk into the red cell layer. The float shown in the drawings has a fluted cross-sectional configuration. This configuration imparts a smaller cross-sectional area to the float 6 so that the observed axial length of the centrifuged blood sample, and particularly the buffy coat, will not be significantly elongated. The flutes 7 on the float 6 will serve to maintain the coaxial relationship with the tube 2. As previously noted a fluted cross-sectional-reduced float is not essential to performing the hematocrit and hemoglobin measurements. In this embodiment, the cross sectional area of the float should preferably be no more than about ⅔ of the cross sectional area of the tube bore.

The blood used for the test must be anticoagulated so that the red blood cells and plasma will separate. This may be accomplished by drawing the blood into an anticoagulant-containing vessel prior to loading the blood into the tube, or by incorporating an anticoagulant, such as heparin, or the like, into the transparent tube itself. This would allow the filling of the tube directly from a finger puncture.

It can be appreciated that this procedure takes no more time and requires no more skill than the measurement of the hematocrit alone. It can also be appreciated that an optical scanner, such as described in U.S. Pat. No. 4,156,570 issued May, 1978 to S. C. Wardlaw; or U.S. Pat. No. 4,558,947, issued Dec. 17, 1985 to S. C. Wardlaw, (both of which are specifically incorporated herein by reference in their entireties) could be used to read the lengths and automatically compute the results. Because this procedure relies upon two primary measurements (length and density), the test does not require standardization.

There are two general embodiments of paraphenalia used to perform the procedure of the invention. The first is as shown in the drawings and described above, and the second is identical to the device described in U.S. Pat. No. 4,077,396 issued Mar. 7, 1978 to S. C. Wardlaw et al (the disclosure of which is specifically incorporated herein by reference in its entirety), in that a buffy coat-expanding float is used. In the latter case, the buoyant effects of the expanded buffy coat layers must be taken into account, however the readings can be computed by a microprocessor which has been appropriately preprogrammed as set forth hereinafter.

When the float is large enough to perform the buffy coat measurements, as described in the aforesaid U.S. patents issued to Wardlaw alone and with others, the buoyant effect that the expanded buffy coat exerts on the float can be compensated for as follows. When such a float is used, the three cellular components of the buffy coat will add to the buoyant forces exerted on the plastic float and must, therefore, be taken into account when calculating the red blood cell density. Therefore the following equation will be used.

$$(D_r - D_f) \times L_r + (D_g - D_f) \times L_g + (D_{lm} - D_f) \times L_{lm} + (D_{pl} - D_f) \times L_{pl} + (D_p - D_f) \times L_p = 0:$$

wherein: $D_p$, $D_r$, $D_f$, $L_p$, $L_r$, and $L_f$ are as identified above;

$L_{pl}$ is the observed length of the float disposed in the platelet layer of the blood sample;

$L_{ml}$ is the observed length of the float disposed in the monocyte/lymphocyte cell layer of the blood sample;

$L_g$ is the obeserved length of the float disposed in the granulocyte cell layer of the blood sample;

$D_g$ is the density of the granulocyte cell layer;

$D_{lm}$ is the density of the lymphocyte/monocyte cell layer; and $D_{pl}$ is the density of the platelet layer.

The instrument which is used is adapted for measuring the white cell component counts, as described in the aforesaid prior art. Thus the microprocessor will have inputted information as described above, and will also have the granulocyte, lymphocyte/monocyte, and platelet densities inputted. During the measurement procedure, the lengths of the float disposed in the granulocyte, lymphocyte/monocyte, and platelet layers will be measured, and thus inputted into the microprocessor. The value of $L_f$ will be calculated by the microprocessor as the difference between the total float length minus the cumulative lengths of the float which are submerged in the red cells, granulocytes, lymphocyte/monocytes, and platelets. $D_r$ can then be calculated by the microprocessor. Once $D_r$ is calculated, the hemoglobin value is determined as set forth in the first example.

This technique was tested by determining the hemoglobin and hematocrit of 100 patients. The results obtained by the invention were virtually identical to those obtained in the hospital laboratory using automated analyzers (relative standard error of 2.7%).

It will be readily appreciated that the procedure of this invention will quickly and easily render the hematocrit and hemoglobin measurements in an anticoagulated whole blood sample. The procedure can be conducted by a relatively unskilled person and can be performed with a single blood sample. The procedure is particularly adapted for use in small clinics and in the physician's office, but can also be used in larger laboratories and hospitals.

Since many changes and variations in the disclosed embodiments of the invention may be made without departing from the inventive concept, it is not intended to limit the invention otherwise than as required by the appended claims.

What is claimed is:

1. A method for measuring the hemoglobin concentration of the red blood cells in a sample of whole anticoagulated blood, said method comprising the steps of:
   (a) providing a transparent tube;
   (b) drawing a sample of the blood into the tube;
   (c) positioning a float member in the tube in the blood sample, said float member being made from a material which will float in the red blood cell layer of the blood sample when the tube is centrifuged with the blood sample and float member disposed therein;
   (d) centrifuging the blood sample, float member, and tube to cause layering out of the red blood cells, white blood cells, and plasma, according to their respective densities;
   (e) measuring the length of a portion of the float member which is submerged below the top of the red blood cell layer; and
   (f) calculating the hemoglobin concentration as a function of the float member length which is submerged below the top of the red blood cell layer.

* * * * *